United States Patent [19]

Donald et al.

[11] Patent Number: 5,145,610
[45] Date of Patent: Sep. 8, 1992

[54] ORGANIC OPTICAL ELEMENTS AND NONLINEAR OPTICAL DEVICES

[75] Inventors: Dennis S. Donald, Mendenhall, Pa.; Gerald R. Meredith, Wilmington, Del.

[73] Assignee: E. I. Du Pont de Nemours and Company, Wilmington, Del.

[21] Appl. No.: 441,590

[22] Filed: Nov. 27, 1989

[51] Int. Cl.$^5$ .......................... G02F 1/00; F21V 9/04
[52] U.S. Cl. .................... 252/583; 252/582; 252/587; 359/243
[58] Field of Search ............ 252/583, 582, 587, 589, 252/299.01; 350/96.13, 96.14, 355; 359/243

[56] References Cited

U.S. PATENT DOCUMENTS

| | | | |
|---|---|---|---|
| 4,818,898 | 4/1989 | Anderson et al. | 307/427 |
| 4,871,236 | 10/1989 | Gemma et al. | 350/355 |
| 4,909,598 | 3/1990 | Ninoyama et al. | 350/96.34 |
| 4,946,261 | 8/1990 | Yaegashi et al. | 350/353 |
| 4,962,979 | 10/1990 | Anderson et al. | 350/1.1 |
| 4,981,614 | 1/1991 | Miyazaki et al. | 252/587 |
| 4,983,318 | 1/1991 | Matsumoto et al. | 252/299.01 |
| 4,987,023 | 1/1991 | Sato | 428/215 |
| 4,992,214 | 2/1991 | Etter et al. | 252/587 |

FOREIGN PATENT DOCUMENTS 1193815  8/1989  Japan .................... 252/582

OTHER PUBLICATIONS

Franken et al., Phys. Rev. Lett., vol. 7, 118–119 (1961).
"Nonlinear Optical Properties of Organic and Polymeric Materials", D. J. Williams, ed., Am. Chem. Soc., Washington, D.C. (1983).
D. J. Williams, Angew. Chem., Int. Ed. Engl., vol. 23, 690 (1984).
"Nonlinear Optical Properties of Organic Molecules and Crystals", vol., D. S. Chemla et al., ed., Academic Press, New York, NY (1987).

Primary Examiner—Robert L. Stoll
Assistant Examiner—C. Harris
Attorney, Agent, or Firm—William H. Hamby

[57] ABSTRACT

Optical elements comprising noncentrosymmetric crystalline organic compounds are provided, that are capable of second harmonic generation. The invention further provides for nonlinear optical devices and modulators incorporating the optical elements.

36 Claims, 1 Drawing Sheet

ORGANIC OPTICAL ELEMENTS AND NONLINEAR OPTICAL DEVICES

FIELD OF THE INVENTION

This invention relates to optical elements from noncentrosymmetric crystalline organic compounds, compositions utilizing such compounds, and the like. More particularly, the invention relates to optical elements generating second harmonic radiation, together with modulators and optical devices incorporating such elements.

BACKGROUND OF THE INVENTION

It has been recognized that certain media having a polarization susceptability provide sensitive ways of manipulating beams of incident electromagnetic radiation. Such media are said to possess nonlinear polarization. The size of the effects attributable to such nonlinear polarization depends on the arrangement of electrically charged particles (electrons, ions and nuclei) within the media. To obtain the highest nonlinear polarization property of a medium, the molecules within the medium must be arranged so that the nonlinear properties of the individual polar molecules within the medium do not cancel each other out.

The nonlinear optical response of a molecule can be described in the dipole approximation by the following expression:

$$\mu = \mu_0 + \alpha \cdot E + \beta \cdot\cdot EE + \gamma \cdot\cdot\cdot EEE + \ldots,$$

where $\mu$ is the total dipole moment which consists of the sum of $\mu_0$, the permanent moment, and the induced moment in the molecule; $\alpha$ is the linear polarizability tensor, and $\beta$ and $\gamma$ are the second- and third-order nonlinear polarizability or hyperpolarizability tensors; $\alpha$, $\beta$ and $\gamma$ quantify the moment induced by E, the local electric field.

To describe an ensemble of molecules, such as a crystal, the macroscopic constitutive relationship should be used:

$$P = P_0 + \chi^{(1)} \cdot E + \chi^{(2)} \cdot\cdot EE + \chi^{(3)} \cdot\cdot\cdot EEE + \ldots,$$

where P is the total polarization density which similarly consists of the sum of $P_0$, the permanent polarization density, and the induced polarization density; $\chi^{(1)}$ is the linear susceptibility tensor, and $\chi^{(2)}$ and $\chi^{(3)}$ are the second- and third-order nonlinear susceptibility tensors; E is the Maxwellian electric field. Second-order nonlinear optical phenomena such as second harmonic generation, sum and difference frequency mixing, parametric processes and electro-optical effects arise, by definition, from the presence of the $\chi^{(2)}$ term.

Franken, et al., Phys. Rev. Lett., Vol. 7, 118-119 (1961), disclose the observation of second harmonic generation upon the passage of a pulsed ruby laser beam through crystalline quartz. They observed the generation of the second harmonic of light, in which light of 694.3 nm wavelength was converted to light of 347.2 nm wavelength. The use of a laser beam remains the only practical way to generate an E large enough to be able to detect the SHG phenomena.

To have a large $\chi^{(2)}$, the ensemble should contain molecules possessing large elements in their $\beta$ tensors and these molecules must be oriented in a fashion which prevents extensive mutual cancellation of their second-order nonlinear polarizability. The extent of cancellation depends on details of molecular alignment. For example, in centrosymmetric crystals this cancellation is complete. Thus it is widely known that to obtain nonvanishing $\chi^{(2)}$ noncentrosymmetric structures are required. Approximate theory of local-field behavior allows the calculation of the projection of molecular nonlinear polarizability, $\beta$, to the macroscopic scale based largely on details of molecular orientation. An important result is that for each crystal class there are optimal tilts of the constituent molecules relative to the crystal axes which maximize various elements of the $\chi^{(2)}$ tensor. Useful reviews of the art relating to nonlinear properties of organic materials are given in the following references: "Nonlinear Optical Properties of Organic and Polymeric Materials", D. J. Williams, ed., American Chemical Society, Washington, D.C. (1983); D. J. Williams, Angew. Chem., Int. Ed. Engl., Vol. 23, 690 (1984); "Nonlinear Optical Properties of Organic Molecules and Crystals", Vol. 1 and 2, D. S. Chemla et al., ed., Academic Press, New York, NY (1987).

Although a large number of organic and inorganic materials capable of SHG have been found since Franken's discovery, an intense search continues. Through many years of research, it is now known that an organic molecule having a conjugated x electron system or a low-lying charge transfer excited state often has a large second-order polarizability. Many molecules with large $\beta$ elements have been discovered based on these principles. However, crystals of many of these molecules have no practical use for second-order nonlinear optical effects because of their small $\chi^{(2)}$ elements. The failure to efficiently project second-order nonlinearity from the molecular to the macroscopic level results from unfavorable alignment of molecules in the structure of the crystals they form. At present the prediction of crystal structures is not a reliable science. Thus the empirical determination of second-order nonlinearity is a key step in the identification of new materials for these applications.

It is an object of the present invention to provide optical elements useful in second harmonic generation. It is a further object of the present invention to provide optical devices, electro-optic modulators and the like incorporating these optical elements. A feature of the present invention is the use of noncentrosymmetric crystalline organic compounds for the optical elements. It is an advantage of the present invention to provide noncentrosymmetric crystalline organic compounds suitable for containment within polymeric binders, glass and the like. These and other objects, features and advantages will become apparent upon bearing reference to the following description of the invention.

SUMMARY OF THE INVENTION

The present invention provides an optical element comprising a noncentrosymmetric crystalline organic compound selected from the group consisting of

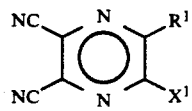

(1)

-continued

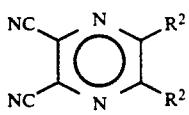

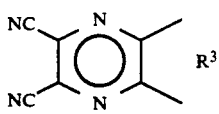

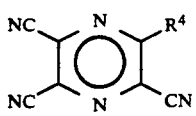

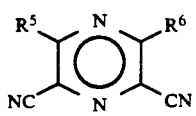

wherein $X^1$ is a halogen selected from the group consisting of Cl and Br;

$R^1$ is selected from the group consisting of halogen, with the proviso that $R^1$ is the same as $X^1$, and

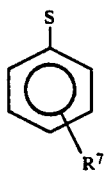

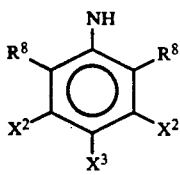

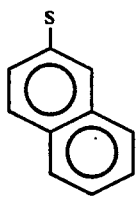

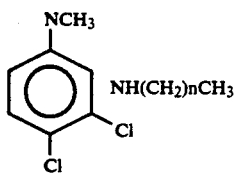

-continued

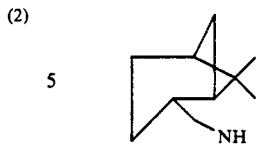

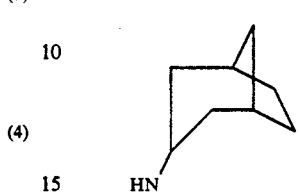

wherein $R^7$ is selected from the group consisting of H, $CH_3$, $CH_2CH_3$, $C(CH_3)_3$, Cl, Br, $OCH_3$, and $NHC(O)CH_3$;

$R^8$ is selected from H and $CH_2CH_3$;

$X^2$ is selected from H, Cl, Br and CN;

$X^3$ is selected from H, Cl, Br and CN;

n=1-4;

$R^2$ is selected from the group consisting of

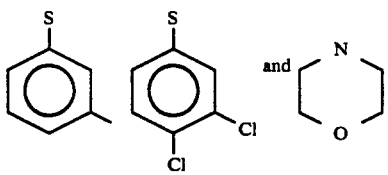

$R^3$ is selected from the group consisting of

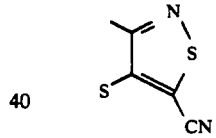

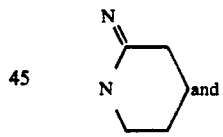

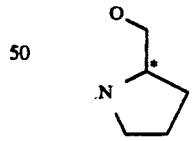

$R^4$ is an amine selected from the group consisting of $N(R^9)_2$

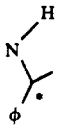

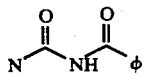

wherein R⁹ is selected from H, CH₃ and CH₂CH₃; and R⁵ and R⁶ are independently chosen from the group consisting of NH₂, OCCl₃, O(CH₂)₂CH₃ and morpholino.

In addition the invention provides for an optical element comprising a noncentrosymmetric crystalline organic compound containing no hydrogens and selected from the group consisting of

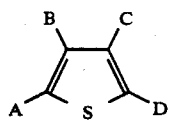 (6)

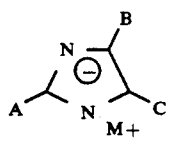 (7)

wherein A, B, C, D are selected from the group of halogens and cyano and M⁺ is selected from the group of Na⁺, K⁺, Li⁺ and Ag⁺.

In addition the invention provides for an optical element comprising a noncentrosymmetric crystalline organic compound selected from the group consisting of

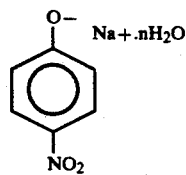

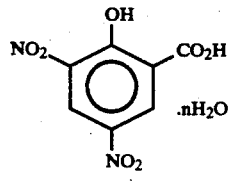

wherein n can be zero to 6, and

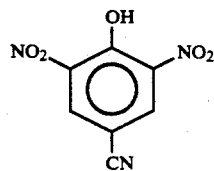

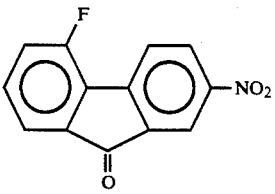

In the case of the nitrophenoxide above, it is preferred that n=2 and in the case of 1-hydroxy-2,4-dinitro benzoic acid it is preferred that n=1.

The invention also provides a method of generating second harmonic radiation using said nonlinear optical element. The invention also provides an electro-optic modulator using said nonlinear optical element. The invention provides, in addition, frequency conversion methods of the sum or difference frequency mixing and parametric generation and parameteric amplification types using said nonlinear optical element. These and other embodiments of the invention will be further discussed with reference to the drawings.

This invention also provides a nonlinear optical device capable of second harmonic generation, wherein the device comprises a source of optical radiation and an optical element selected from those specified above The nonlinear optical device of the invention comprises means to direct at least one incident beam of electromagnetic radiation into the nonlinear optical element, i.e. optical element having nonlinear optical properties, whereby electromagnetic radiation emerging from said element contains at least one frequency different from the the frequency of any incident beam of radiation; said nonlinear optical element selected from those specified above.

The electro-optic modulator of the invention comprises means to direct a coherent beam into an optical element, and means to apply an electric field to said element in a direction the transmission properties of said beam, said element selected from those specified above.

BRIEF DESCRIPTION THE DRAWINGS

DETAILED DESCRIPTION OF THE INVENTION

The nonlinear optical element in accordance with the present invention is preferably a noncentrosymmetric crystalline cyanopyrazine, i.e. a cyanopyrazine which is crystallized in a noncentrosymmetric space group, and is preferrably selected from the group consisting of a compound of formula (1) wherein

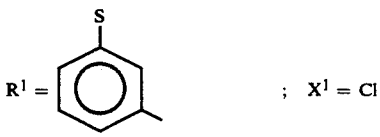

-continued
$R^1 =$ 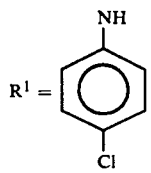 ; $X^1 = Cl$
$R^1 =$ 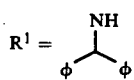 ; $X^1 = Cl$
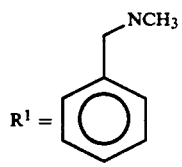 ; $X^1 = Cl$
$R^1 =$ 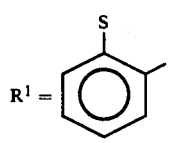 ; $X^1 = Cl$
$R^1 =$ 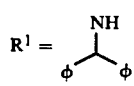 ; $X^1 = Br$
$R^1 =$ 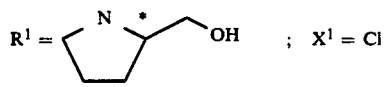 ; $X^1 = Cl$
$R^1 =$ 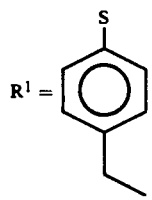 ; $X^1 = Cl$
$R^1 =$ 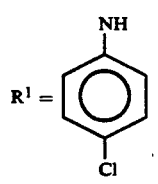 ; $X^1 = Br$
$R^1 =$ 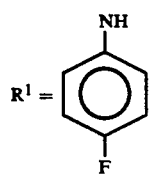 ; $X^1 = Cl$
$R^1 =$ 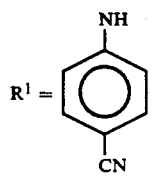 ; $X^1 = Br$
$R^1 =$ 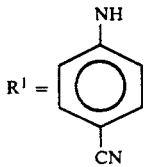 ; $X^1 = Cl$
$R^1 =$ 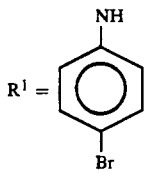 ; $X^1 = Cl$
$R^1 =$ 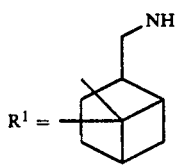 ; $X^1 = Cl$
$R^1 =$ 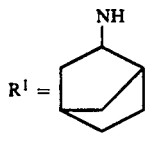 ; $X^1 = Cl$
$R^1 =$ 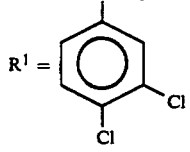 ; $X^1 = Cl$
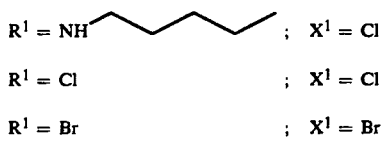
$R^1 = NH$  ; $X^1 = Cl$
$R^1 = Cl$ ; $X^1 = Cl$
$R^1 = Br$ ; $X^1 = Br$
a compound of formula (2) wherein
$R^2 =$ 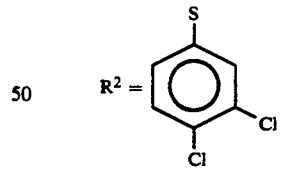
$R^2 =$ 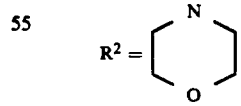
a compound of formula (3) wherein
$R^3 =$ 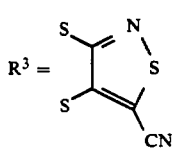

$R^3 =$ 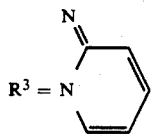

$R^3 =$ 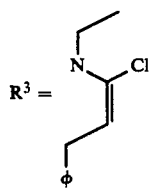

$R^3 =$ 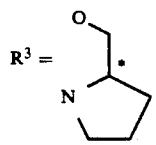

a compound of formula (4) wherein $R^4 =$ 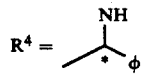

$R^4 =$ NH$_2$ $R^4 =$ N(CH$_3$)$_2$ $R^4 =$ 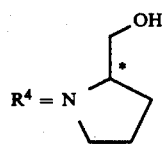

$R^4 =$ 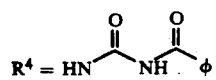

a compound of formula (5) wherein $R^5 =$ NH$_2$; $R^6 =$ 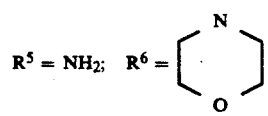

$R^5 =$ O(CH$_2$)$_2$CH$_3$; $R^6 =$ O(CH$_2$)$_2$CH$_3$ $R^5 =$ O(CCl$_3$); $R^6 =$ O(CCl$_3$)

Also preferred are nonlinear elements comprising a crystalline hydrogen-free organic compound which is crystallized in a noncentrosymmetric space group and is preferably selected from the group consisting of a compound of formula (1) wherein $R^1 =$ Cl; $X^1 =$ Cl $R^1 =$ Br; $X^1 =$ Br a compound of formula (3) wherein $R^3 =$ 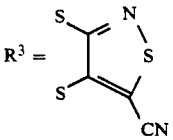

a compound of formula (5) wherein $R^5 =$ O(CCl$_3$); $R^6 =$ O(CCl$_3$)

a compound of formula (6) wherein

A, B, C, D = Br a compound of formula (7) wherein

A = Br; B, C = cyano; M$^+$ = K$^+$

The optical element in accordance with the invention is preferably a single crystal having at least one dimension of about 0.5 mm or greater, but can be substantially smaller crystals imbedded in a film of polymer or in a glass. The smaller crystals can be randomly oriented or aligned with some degree of common orientation, and are preferably aligned. For the smaller crystals, if their size is small enough to prevent light scattering, they can be dispersed in the polymeric binder and pressed, molded or shaped into an optically clear element capable of SHG (second harmonic generation) and other second-order nonlinear optical processes. In some cases the polymer binder should be chosen to be a nonsolvent for the organic compound. For larger crystallites, similar elements can be prepared if the binder used has an index of refraction close to the crystal so as to minimize light scatter and remain transparent.

Figure 1:
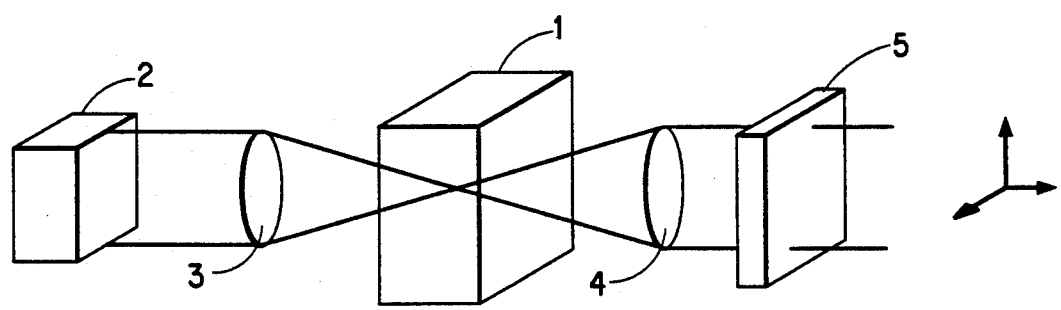
FIG. 1 is a plan view a nonlinear optical device according to the invention.

The use of the optical elements in accordance with the invention is illustrated by reference to the drawings. Referring to FIG. 1 nonlinear optical element 1 is oriented in one of a potentially infinite number of crystal orientations which achieve at least partially maximized SHG (second harmonic generation) conversion by virtue of phase matching. The specific orientation is chosen for reasons of noncriticality, maximum nonlinearity, increased angular acceptance, etc. Polarized light of wavelength 1.05 μ from laser 2 is incident on the optical element along the optical path. Preferably, the electromagnetic radiation, e.g. polarized light, is radiation from one of a number of common lasers, such as Nd-YAG,YLF or glass, semiconductor diode, Er-Glass, Ti-Sapphire, dye, and Ar or Kr ion or radiation shifted to other frequencies by nonlinear processes. A lens 3 focuses the light onto the optical element 1. Emerging light from optical element 1 is collimated by a similar lens 4 and passed through a filter 5 adapted to remove light of initial wavelength, e.g., 1.05 μ, while passing light of a different wavelength, e.g., 0.525 μ. Preferably, the emerging radiation of a different frequency is doubled (second-order) (SHG).

Figure 2:
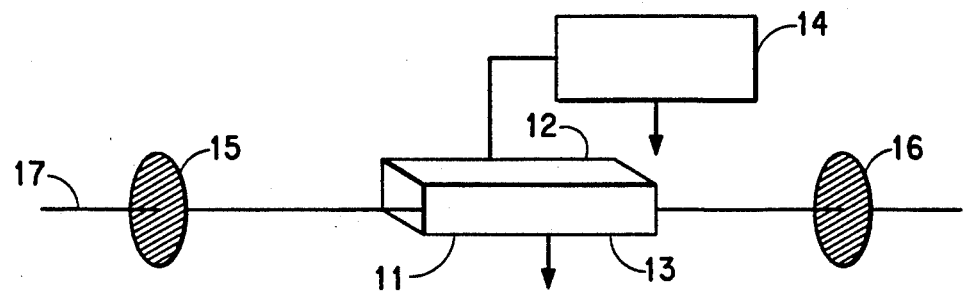
FIG. 2 is a plan view of an electo-optical modulator of the invention.

Referring to FIG. 2, an electro-optic modulator embodying the invention utilizes optical element 11. A pair of electrodes 12 and 13 are attached to the upper and lower surfaces of optical element 11, across which a modulating electric field is applied from a conventional voltage source 14. Optical element 11 is placed between polarizers 15 and 16. A light beam 17, such as that from an Nd-YAG laser, is polarized by polarizer 15, focused on the optical element 11, propagated through the crystal or crystals and subjected to modulation by the electric field. The modulated light beam is led out through polarizer 16. Linearly polarized light traversing optical element 11 is rendered elliptically polarized by action of the applied modulating voltage. Polarizer 16 renders the polarization linear again. Application of the modulating voltage alters the birefringence of optical element 11 and consequently the ellipticity impressed on the beam. Polarizer 16 then passes a greater or lesser fraction of the light beam as more or less of the elliptically polarized light projects onto its nonblocking polarization direction.

It is understood that the invention has been described with reference to preferred embodiments thereof and that variations are to be included within the scope of the invention. Furthermore, frequency or phase modulation of the light beam by the modulator is possible, although the embodiment specifically described performs intensity modulation.

It will be further apparent to those skilled in the art that the optical element of the invention is useful in other devices utilizing their nonlinear properties, such as sum and difference frequency mixing, parametric generation and amplification, and the electro-optic effect. The use of crystals having nonlinear optical properties in optical devices is known in the art, as shown by U.S. Pat. Nos. 3,747,002, 3,328,723, 3,262,058 and 3,949,323.

The invention is further illustrated by the following Example.

EXAMPLES

For the compounds shown in Table 1 SHG was measured by the powder method of Kurtz, et al., J. Appl. Phys., Vol. 39, 3798 (1968), using a Nd-Glass laser ($\lambda = 1.05$ μm) and quartz as a reference. The crystalline quartz powder used as a reference had an average particle size of 30 μm. The intensity of the second harmonic radiation generated by the samples was thus measured relative to that provided by quartz.

TABLE 1

| COMPOUND | SHG × O | SOLVENT OF CRYSTALLIZATION |
|---|---|---|
| [structure] | 10,000 | n-Butyl Chloride |
| [structure] | 6,500 | Acetonitrile |
| [structure] | 4,200 | Nitromethane |
| [structure] | 650 | n-Butyl Chloride |

TABLE 1-continued

| COMPOUND | SHG × O | SOLVENT OF CRYSTALLIZATION |
|---|---|---|
| | 330 | n-Butyl Chloride |
| | 500 | Toluene |
| | 343 | i-Propanol |
| | 170 | 1:1 Ethylacetate/ Petroleum Ether |
| | 70 | Benzene |
| | 125 | 1:1 Methylene Chloride/Carbon Tetrachloride |

TABLE 1-continued

| COMPOUND | SHG × O | SOLVENT OF CRYSTALLIZATION |
|---|---|---|
| (pyrazine with two CN groups and two (3,4-dichlorophenyl)thio substituents) | 2,700 | Aqueous Ethanol |
| (isothiazole-CN linked via two S to pyrazine-dicarbonitrile) | 8,400 | 1,2-Dichloroethane |
| (pyridine fused imidazo-pyrazine dicarbonitrile) | 100 | Acetonitrile |
| (4-ethylphenylthio, chloro-substituted pyrazine dicarbonitrile) | 200 | n-Hexane |
| (amino-tricyano pyrazine) | 200 | Chloroform |
| (4-chloroanilino, bromo pyrazine dicarbonitrile) | 1,700 | Toluene |
| (4-fluoroanilino, chloro pyrazine dicarbonitrile) | 2,900 | Acetonitrile |

TABLE 1-continued

| COMPOUND | SHG × O | SOLVENT OF CRYSTALLIZATION |
|---|---|---|
| (structure) | 100 | Acetonitrile |
| (structure) | 60 | Acetonitrile |
| (structure) | 10,000 | Acetonitrile |
| (structure) | 260 | n-Hexane |
| (structure) | 430 | Acetonitrile |
| (structure) | 125 | 1-Chlorobutane |
| (structure) | 100 | Benzene |

TABLE 1-continued

| COMPOUND | SHG × O | SOLVENT OF CRYSTALLIZATION |
|---|---|---|
| | 500 | Chloroform |
| | 330 | 1-Chlorobutane |
| | 650 | Acetonitrile |
| | 230 | Acetonitrile |
| | 200 | 1-Chlorobutane |
| | 170 | 1-Chlorobutane |
| | 133 | Carbon Tetrachloride/ Chloroform |

TABLE 1-continued

| COMPOUND | SHG × O | SOLVENT OF CRYSTALLIZATION |
|---|---|---|
| [structure: pyrazine with NC, CN, NH-CO-NH-CO-φ] | 66 | Tetrahydrofuran |
| [structure: pyrazine with CN groups and OCCl3 groups] | 10 | Carbon Tetrachloride |
| [structure: Br-imidazole anion with CN groups, K+] | 13 | t-Butyl Alcohol |
| [structure: 3,5-dinitro-4-hydroxybenzonitrile] | 730 | Ethanol |
| [structure: nitro-fluoro-fluorenone] | 2,300 | Acetone |
| 3,5-Dinitrosalicyclic Acid Monohydrate | 1,000 | Water |
| Sodium 4-Nitrophenoxide | 4,200 | Ethanol |
| Tetrabromothiophene | 100 | n-Hexane |

We claim:

1. An optical element comprising a noncentrosymmetric crystalline organic compound selected from the group consisting of

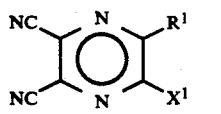 (1)

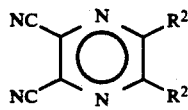 (2)

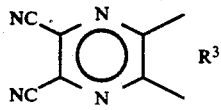 (3)

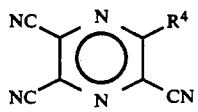 (4)

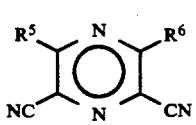 (5)

wherein
 $X^1$ is a halogen selected from the group consisting of Cl and Br;
 $R^1$ is selected from the group consisting of halogen, with the proviso that $R^1$ is the same as $X^1$, and

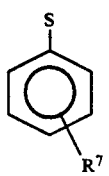

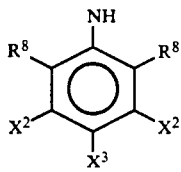

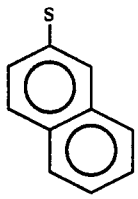

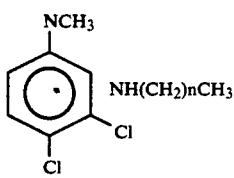

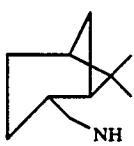

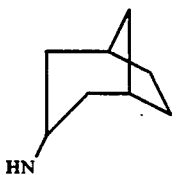

wherein $R^7$ is selected from the group consisting of H, $CH_3$, $CH_2CH_3$, $C(CH_3)_3$, Cl, Br, $OCH_3$, and $NHC(O)CH_3$;

$R^8$ is selected from H and $CH_2CH_3$;

$X^2$ is selected from H, Cl, Br and CN;

$X^3$ is selected from H, Cl, Br and CN;

n=1-4;

$R^2$ is selected from the group consisting of

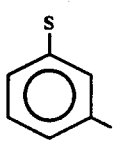 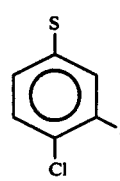 and 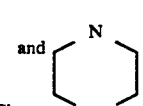

$R^3$ is selected from the group consisting of

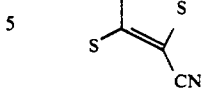

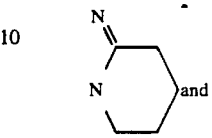

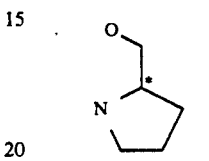

$R^4$ is an amine selected from the group consisting of

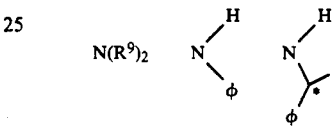

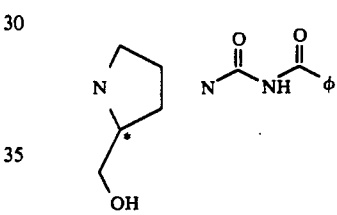

wherein $R^9$ is selected from H, $CH_3$ and $CH_2CH_3$; and $R^5$ and $R^6$ are independently chosen from the group consisting of $NH_2$, $OCCl_3$, $O(CH_2)_2CH_3$ and morpholino.

2. An optical element comprising a noncentrosymmetric crystalline organic compound containing no hydrogens and selected from the group consisting of

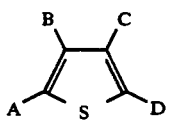 (6)

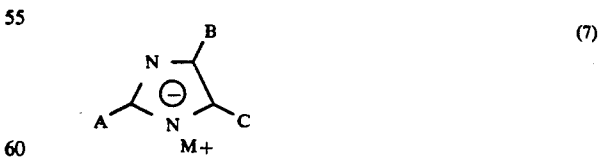 (7)

wherein A, B, C, D are selected from the group consisting of halogens and cyano and M+ is selected from the group consisting of Na+, K+, Li+ and Ag+.

3. An optical element consisting of a noncentrosymmetric crystalline organic compound selected from the group consisting of

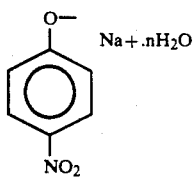

and

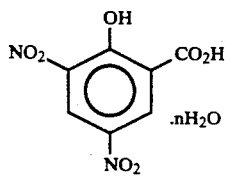

wherein n is 0 to 6, and

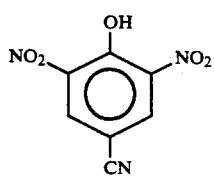

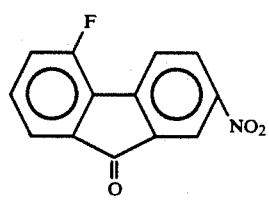

4. An optical element consisting of the noncentrosymmetric crystalline organic compound

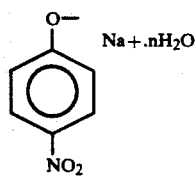

wherein n is 2.

5. The optical element of claim 3 wherein the organic compound if 1-hydroxy-2,4-dinitrobenzoic acid and n is 1.

6. The optical element of claim 1 wherein the organic compound is (1) and $R^1$ is selected from the group consisting of

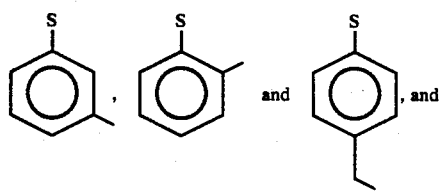

$X^1$ is Cl.

7. The optical element of claim 1 wherein the organic compound is (1) and $R^1$ is selected from the group consisting of

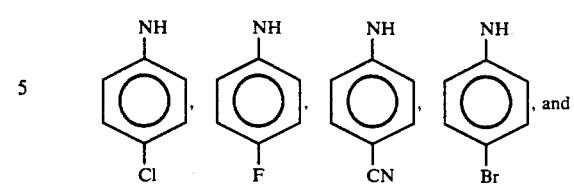

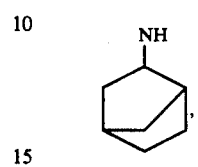

and $X^1$ is Cl.

8. The optical element of claim 1 wherein the organic compound is (1) and $R^1$ is selected from the group consisting of

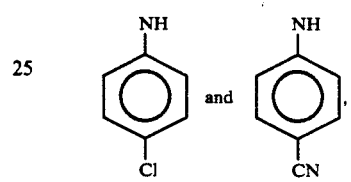

and $X^1$ is Br.

9. The optical element of claim 1 wherein the organic compound is (1) and $R^1$ is

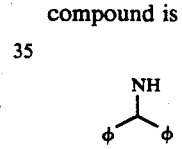

and $X^1$ is Cl or Br.

10. The optical element of claim 1 wherein the organic compound is (1U) and $R^1$ is selected from the group consisting of

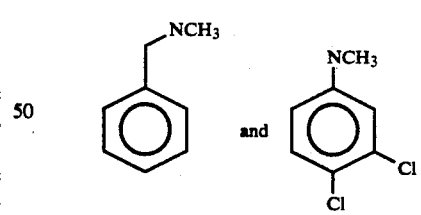

and $X^1$ is Cl.

11. The optical element of claim 1 wherein the organic compound is (1) and $R^1$ is

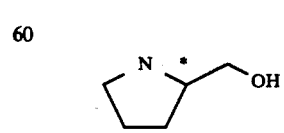

and $X^1$ is Cl.

12. The optical element of claim 1 wherein the organic compound is (1) and $R^1$ is

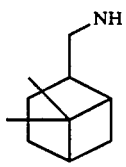

and X¹ is Cl.

13. The optical element of claim 1 wherein the organic compound is (1) and R¹ is

and X¹ is Cl.

14. The optical element of claim 1 wherein the organic compound is (1) and R¹ and X¹ are Cl.

15. The optical element of claim 1 wherein the organic compound is (1) and R¹ and X¹ are Br.

16. The optical element of claim 1 wherein the organic compound is (2) and R² is

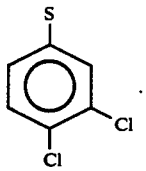

17. The optical element of claim 1 wherein the organic compound is (2) and R² is

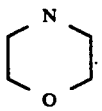

18. The optical element of claim 1 wherein the organic compound is (3) and R³ is

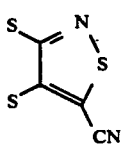

19. The optical element of claim 1 wherein the organic compound is (3) and R³ is

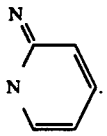

20. The optical element of claim 1 wherein the organic compound is (3) and R³ is

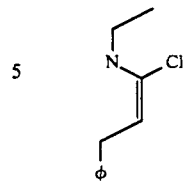

21. The optical element of claim 1 wherein the organic compound is (3) and R³ is

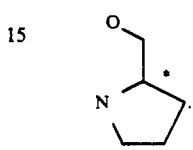

22. The optical element of claim 1 wherein the organic compound is (4) and R⁴ is

23. The optical element of claim 1 wherein the organic compound is (4) and R⁴ is $NH_2$.

24. The optical element of claim 1 wherein the organic compound is (4) and R⁴ is $N(CH_3)_2$.

25. The optical element of claim 1 wherein the organic compound is (4) and R⁴ is

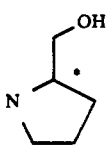

26. The optical element of claim 1 wherein the organic compound is (4) and R⁴ is

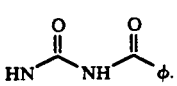

27. The optical element of claim 1 wherein the organic compound is (5) and R⁵ is $NH_2$ and R⁶ is

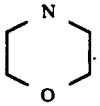

28. The optical element of claim 1 wherein the organic compound is (5) and R⁵ is $O(CH_2)_2CH_3$ and R⁶ is $O(CH_2)_2CH_3$.

29. The optical element of claim 1 wherein the organic compound is (5) and R⁵ is $O(CCl_3)$ and R⁶ is $O(CCl_3)$.

30. A nonlinear element comprising a crystalline hydrogen-free organic compound which is crystallized in a noncentrosymmetric space group and is

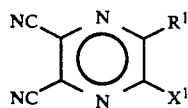

wherein $R^1$ and $X^1$ are identically Cl or Br.

31. A nonlinear element comprising a crystalline hydrogen-free organic compound which is crystallized in a noncentrosymmetric space group and is

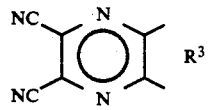

wherein $R^3$ is

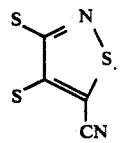

32. A nonlinear element comprising a crystalline hydrogen free organic compound which is crystallized in a noncentrosymmetric space group and is

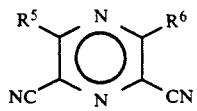

wherein $R^5$ and $R^6$ are $O(CCl_3)$.

33. A nonlinear element comprising a crystalline hydrogen-free organic compound which is crystallized in a noncentrosymmetric space group and is

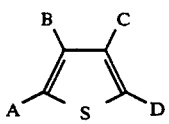

wherein A, B, C, and D are Br.

34. A nonlinear element comprising a crystalline hydrogen-free organic compound which is crystallized in a noncentrosymmetric space group and is

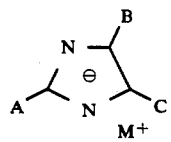

wherein A is Br, B and C are cyano, and $M^+$ is $K^+$.

35. The optical element of claim 1 in the form of a single crystal having at least one dimension of at least about 0.5 mm.

36. The optical element of claim 1 wherein the noncentrosymmetric crystalline organic compound is dispersed in a polymer or glass.

* * * * *